United States Patent
Brady et al.

(10) Patent No.: US 7,118,653 B2
(45) Date of Patent: *Oct. 10, 2006

(54) PROCESS FOR THE PURIFICATION OF MIXTURES OF TOLUENEDIISOCYANATE INCORPORATING A DIVIDING-WALL DISTILLATION COLUMN

(75) Inventors: Bill Brady, Düsseldorf (DE); Friedhelm Steffens, Leverkusen (DE); Berthold Keggenhoff, Krefeld (DE); Kai Verkerk, Hilden (DE); Gerhard Ruffert, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 242 days.

This patent is subject to a terminal disclaimer.

(21) Appl. No.: 10/457,307

(22) Filed: Jun. 9, 2003

(65) Prior Publication Data
US 2003/0230476 A1   Dec. 18, 2003

(30) Foreign Application Priority Data
Jun. 14, 2002   (EP)   ................... 02013460

(51) Int. Cl.
B01D 3/14 (2006.01)
C07C 263/20 (2006.01)
C07C 263/10 (2006.01)
C07C 265/10 (2006.01)

(52) U.S. Cl. .................... 203/29; 203/71; 203/100; 560/347; 560/352; 560/359

(58) Field of Classification Search ............. 203/29, 203/71, 100; 560/347, 352, 359; 196/111; 202/158
See application file for complete search history.

(56) References Cited

U.S. PATENT DOCUMENTS
2,471,134 A   5/1949   Wright ................. 196/100
(Continued)

FOREIGN PATENT DOCUMENTS
GB   1 173 890   * 12/1969
(Continued)

OTHER PUBLICATIONS

Polyurethane Handbook (Oertel G. (editor), Polyurethane Handbook, Munich Germany: Hanser Publishers, (month unavailable) 1985, pp. 62-73, "Isocyanates" Dr. K. Schauerte.

Industrielle Aromatenchemie (Franck H.-G and Stadelhofer J., Aromatenchemie, Berlin, Germany, Springer Verlag, (month unavailable) 1987"Herstellung und Verwendung on Toluel-Derivaten", p. 253.

Chem. System's PERP Report for TDI/MDI (Chem. Systems, Process Evaluation Research Planning TDI/MDI 99/99S8. Tarrytown, NY, USA: Chem. Systems (month unavailable) 1999, pp. 27-32.

(Continued)

*Primary Examiner*—Virginia Manoharan
(74) *Attorney, Agent, or Firm*—Joseph C. Gil; Lyndanne M. Whalen

(57) ABSTRACT

Process for the purification of toluenediisocyanate from a crude distillation feed which includes toluenediisocyanate, an organic solvent and less than 2% by weight phosgene by separating the crude distillation feed in a dividing-wall distillation column into at least four product fractions P1–P4.

P1 is a phosgene enriched low-boiler product,
P2 is a solvent-enriched product,
P3 is a high boiler enriched bottoms and
P4 is a toluenediisocyanate product stream.

9 Claims, 3 Drawing Sheets

U.S. PATENT DOCUMENTS

| | | | |
|---|---|---|---|
| 2,908,704 A * | 10/1959 | Skiles | 560/347 |
| 3,287,387 A * | 11/1966 | Denton et al. | 560/347 |
| 3,321,283 A * | 5/1967 | Ewald | 422/225 |
| 3,499,021 A * | 3/1970 | Kober et al. | 560/347 |
| 3,987,075 A * | 10/1976 | Schnabel | 560/352 |
| 4,076,577 A * | 2/1978 | Hetzel et al. | 159/47.1 |
| 4,745,210 A * | 5/1988 | Mita et al. | 560/41 |
| 4,851,570 A | 7/1989 | Zaby et al. | 560/347 |
| 5,449,818 A | 9/1995 | Biskup et al. | 560/347 |
| 5,849,947 A * | 12/1998 | Biskup et al. | 560/347 |
| 6,713,630 B1 * | 3/2004 | Rust et al. | 548/228 |
| 6,846,389 B1 * | 1/2005 | Kaibel et al. | 203/1 |

FOREIGN PATENT DOCUMENTS

| | | | |
|---|---|---|---|
| GB | 1 196 008 | * | 6/1970 |
| WO | 01/85708 | * | 11/2001 |

OTHER PUBLICATIONS

Ing. Eng. Chem. Res., 37, (month unavailable) 1998, pp. 3444-3454, Rakesh Agrawal and Zbigniew T. Fidkowski, "Are Thermally Couple Distillation Columns Always Thermodynamically More Efficient for Ternary Distallations".

* cited by examiner

PROCESS FOR THE PURIFICATION OF MIXTURES OF TOLUENEDIISOCYANATE INCORPORATING A DIVIDING-WALL DISTILLATION COLUMN

CROSS REFERENCE TO RELATED PATENT APPLICATION

The present application claims the right of priority under 35 U.S.C. §119 (a)–(d) of European Patent Application No. 02013460.7, filed Jun. 14, 2002.

FIELD OF THE INVENTION

The present invention relates to an improvement of a toluenediisocyanate (TDI) recovery and purification process which uses a dividing-wall distillation column to recover the toluenediisocyanate from a crude isocyanate stream. Further, the dividing-wall distillation column used in the purification process can be designed to enable energy efficient operation for various feed rates, compositions and product specifications. The process of the present invention benefits from the ability to achieve a lower total manufacturing cost.

BACKGROUND OF THE INVENTION

The present invention relates to a process wherein toluenediamine is reacted with phosgene in the presence of a solvent solution in the liquid phase or wherein toluenediamine is reacted with phosgene directly in the gas phase with a solvent used in the quench cooling of said reaction; excess phosgene is then partially or completely removed from the resulting reaction mixture and the dephosgenated crude distillation feed fed to a fractionation process including a dividing-wall distillation column wherein four fractions are recovered:

1. a phosgene-enriched low-boiler product, which is recovered and returned to the dephosgenation or excess phosgene recovery process,
2. a relatively pure solvent product (less than 100 ppm by weight TDI) which is then reused in the phosgenation or excess phosgene recovery process,
3. a high-boiler (polymeric isocyanate, hydrolyzable chloride compounds (HCC), and other non-volatiles) enriched bottoms product which is sent to a residue removal system for the further recovery of volatiles,
4. a toluenediisocyanate product stream.

The field of art to which this invention pertains is a process for the purification of toluenediisocyanate (TDI) mixtures. TDI mixtures are generally produced by reacting toluene with nitric acid to yield dinitrotoluene (DNT), hydrogenating the resultant dinitrotoluene (DNT) to yield toluenediamine (TDA) and reacting the toluenediamine (TDA) with phosgene to give toluenediisocyanate (TDI). Toluenediisocyanate (TDI) is a commercial available material particularly useful in the preparation of polyurethanes, polyurea and polyisocyanurate polymers, especially foamed polymers.

DE-A1-37 36 988 teaches that organic mono- or polyisocyanates are continuously prepared by reacting the corresponding mono- or polyamine dissolved in an inert organic solvent with phosgene also dissolved in an inert organic solvent at a temperature under 150° C. The amine and phosgene solutions are combined and allowed to pass through one or more reaction columns connected below to above in series and having at least 10 chambers in total separated from each other by perforated plates, the holes of which preferably have a maximum diameter of 20 mm.

EP-A1-5 70 799 teaches that production of aromatic diisocyanates is effected by reaction of diamines and phosgene. The phosgene and diamine are at above the boiling temperature of the diamine and the reaction has an average contact time of 0.5–5 seconds. The mixture is continuously passed through a cylindrical reaction space at 200–600° C. to complete the reaction with avoidance of back mixing. The gas mixture is then cooled to condense the diisocyanates, with the temperature being maintained above the decomposition temperature of carbamic acid chlorides corresponding to the diamines used. Uncondensed diisocyanates is washed out of the gas mixture with an inert solvent, and the inert solvent is recovered by distillation.

The *Polyurethane* Handbook (Oertel, G. (Editor), Polyurethane Handbook, Munich, Germany: Hanser Publishers, 1985, pp 62–73) gives a description of a state of the art for the phosgenation and distillation process for the production of toluenediisocyanate. In the distillation process, the solvent is completely removed from the crude TDI mixture as the top product from a solvent column, with this solvent being returned to the phosgenation or to the excess phosgene recovery. The remaining crude isocyanate bottoms stream from the solvent column is sent to a pre-flasher where two products are achieved: a isocyanate rich overhead product and a residue-enriched bottoms stream which is fed to the residue removal. In the residue removal, the volatiles are then removed from this residue-enriched stream and condensed. The condensed volatiles from residue removal together with the condensed overhead stream from the pre-evaporation are then combined and fed to an isocyanate column. In the isocyanate column, the product isocyanate is recovered as a top stream while a high-boiler enriched bottoms stream is returned to the pre-evaporation step. This process is limited by the fact that the complete solvent removal is performed in one solvent column. While it is known that TDI yields are negatively affected by higher temperatures, complete solvent removal necessitates operating under relatively low pressures to achieve sump temperatures low enough to prevent a loss of yield, thus necessitating a large column.

Moreover, the long residence-time of isocyanate together with residue in heating zones can lead to a higher rate of residue formation. Finally, condensation of the overhead stream from the pre-evaporation before feeding to the isocyanate column is energy inefficient.

In *Industrielle Aromatenchemie* (Franck H.-G. and Stadelhofer J., Industrielle Aromatenchemie. Berlin, Germany: Springer Verlag, 1987, p. 253) a second state-of-the-art process is described. In the described process, the crude TDI-solvent mixture is fed to a two-step pre-evaporation step resulting in a low-boiling overhead vapor product and solvent-free residue-enriched bottoms product which is fed to the residue removal. In the residue removal process, the volatiles are then removed from this residue-enriched stream and condensed. The overhead product from the pre-evaporation is fed to a solvent column. In the solvent column the solvent is completely removed as the top product, with the solvent being returned to the phosgenation or to the excess phosgene recovery. The remaining crude isocyanate bottoms stream from the solvent column is fed along with the condensed volatiles from residue removal to an isocyanate column. In the isocyanate column, the product isocyanate is recovered as a top stream while a high-boiler (polymeric isocyanate and hydrolyzable chloride compounds (HCC), and other non-volatiles) enriched bottoms stream is returned to the pre-evaporation step. This process is also limited by the fact that the complete solvent removal must be performed in one solvent column. As in the process described in the *Polyurethane Handbook*, complete solvent removal necessitates operating under relatively low pressures to achieve sump temperatures low enough to prevent a loss of yield, resulting in a large solvent column. However, this process, in comparison with the former process achieves a reduced residence-time of isocyanate together with residue in heating zones possibly leading to a lower rate of residue formation. Moreover, because there is no needless condensation of a vapor feed to the isocyanate column, this process will be more energy efficient.

From Chem System's *PERP Report for TDI/MDI* (Chem Systems, Process *Evaluation* Research Planning TDI/MDI 98/99S8. Tarrytown, N.Y., USA: Chem Systems, 1999, pp 27–32) for TDI/MDI it can be learned, that the fractionation of a crude TDI distillation feed product can be completed in the following manner. Normally, the liquid product from the dephosgenation stage is sent to a pre-evaporator which produces a residue-rich liquid-phase as a bottom product and a vapor-phase product containing mainly solvent and isocyanate as an overhead product. The bottom product from the pre-evaporation is sent to a process for the removal of volatile compounds from the reaction residues (residue removal). The volatile components removed in the residue removal stage as well as the vapor-phase product from the pre-evaporator are sent to a solvent column, where an initial separation of the isocyanate from solvent is completed as well as the removal of any remaining phosgene. The resulting products are a phosgene-enriched top product, a relatively pure solvent stream as an intermediate product and an isocyanate-enriched bottoms product. The phosgene stream is then returned to the dephosgenation process or to the excess phosgene recovery process. The solvent product is then used in the phosgenation section as well as in the excess phosgene recovery. The bottoms isocyanate-rich product is then sent to a second solvent removal column where the remainder of the solvent is removed. The top solvent product from this step, when relatively pure, can be used in phosgenation or excess phosgene recovery or can be returned to the primary solvent removal step. The final solvent-free bottoms isocyanate product is sent to an isocyanate column, resulting in an isocyanate top product and a residue and hydrolyzable chloride compound (HCC) enriched-bottom stream which is returned to the pre-evaporation or to the residue-removal stages. This process like the process described in *Industrielle Aromatenchemie*, in comparison with the process described in the *Polyurethane Handbook* achieves a reduced residence time of isocyanate together with residue in heating zones possibly leading to a lower rate of residue formation. Additionally, like the process described in *Industrielle Aromatenchemie*, because there is no needless condensation of a vapor feed to the isocyanate column, this process will be more energy efficient than the process disclosed in the Polyurethane Handbook. It holds the additional advantage, that the solvent removal is completed in two steps. By taking advantage that the solvent has a lower boiling point than the isocyanate, the majority of the solvent can be removed under higher pressure, therefore, reducing the necessary investment cost for the solvent removal. Additionally, the use of two solvent removal steps adds to the flexibility of operation. However, the presence of a third column adds more complexity to the process.

In fractionation, it is sometimes desirable to separate a multi-component feed stream into a number of streams containing, various fractions of desirable components in the product streams. For the case of one feed stream and two product streams, the separation can be accomplished by distillate and bottoms product draw. Further separation can be accomplished by repeating the two-product stream process to either the distillate or the bottoms streams. However, the introduction of additional columns will require a corresponding number of reboilers and condensers. That requirement, in turn, requires additional operating costs as the condensing and the reboiling process is being repeated. Numerous references can be found in prior art documenting efforts to lower both capital and operating costs in the separation of several fractions from a multi-component feed stream. The benchmark of the lowest energy consumption has been set by the old and well-known PETLYUK system (Agrawal, R and Fidkowski, Z, Are Thermally Coupled Distillation Columns Always Thermo-dynamically More Efficient for Ternary Distillations?, Industrial & Engineering Chemistry Research, 1998, 37, pp 3444–3454). In this configuration, a prefractionation column separates the feed into two streams using a split vapor stream from the main column's stripping section and a split liquid stream from the main column's rectifying section. The resulting vapor and liquid streams exiting from the prefractionation column are richer in light and heavy components respectively. These two semi-processed streams are then fed back to the main column. This configuration provides an advantage allowing the main fractionation column to enhance the purity of the side stream draw. In turn, the main fractionation column also provides the stripping section and the rectifying section with better quality feeds. The combined effect is a very efficient use of vapor/liquid traffic to yield three product streams.

U.S. Pat. No. 2,471,134 teaches an improvement of the Petyluk process with a proposition to combine the prefractionation and main columns into one fractionation unit by erecting a partition along the center part of a column. The column is equipped with one overhead condenser and one bottom reboiler.

The dividing-wall distillation column according to U.S. Pat. No. 2,471,134 is a vertical column fractionating tower, equipped with reboiler and condenser, which is divided into four distinct column sections by the use of a center partition in the intermediate part of the column. These sections are a common bottom (stripping) and top (rectifying) sections, and the prefractionation and main fractionation sections in the intermediate part of the column separated by a dividing-wall. The multi-component mixture is fed to the prefractionation section, the overhead product is taken from the common rectifying section, a bottoms product is taken from the common stripping section, and the intermediate product stream is taken as a side-product from the main fractionation section.

This dividing-wall distillation column is effective in overcoming the hydraulic limitations in the PETLYUK system. At the same time, it reduces capital costs by having only one common shell. The dividing-wall distillation column disclosed in U.S. Pat. No. 2,471,134 has found applications in several processes.

Generally, the development of the process for TDI recovery has resulted in reductions in capital investment, greater energy efficiency, and improved product yield. But, the energy consumption, capital investment and product yield is still insufficient.

BRIEF SUMMARY OF THE INTENTION

In the present invention, the use of the dividing-wall distillation column in the relatively complex TDI distillation process allows for a surprising reduction in the energy required to complete this process while at the same time reducing investment costs. Moreover the process provides the potential to shorten the residence time that the product remains with the high-boiler fraction in heated zones, which will subsequently lead to better product yields.

DETAILED DESCRIPTION OF THE INVENTION

Figure 1:
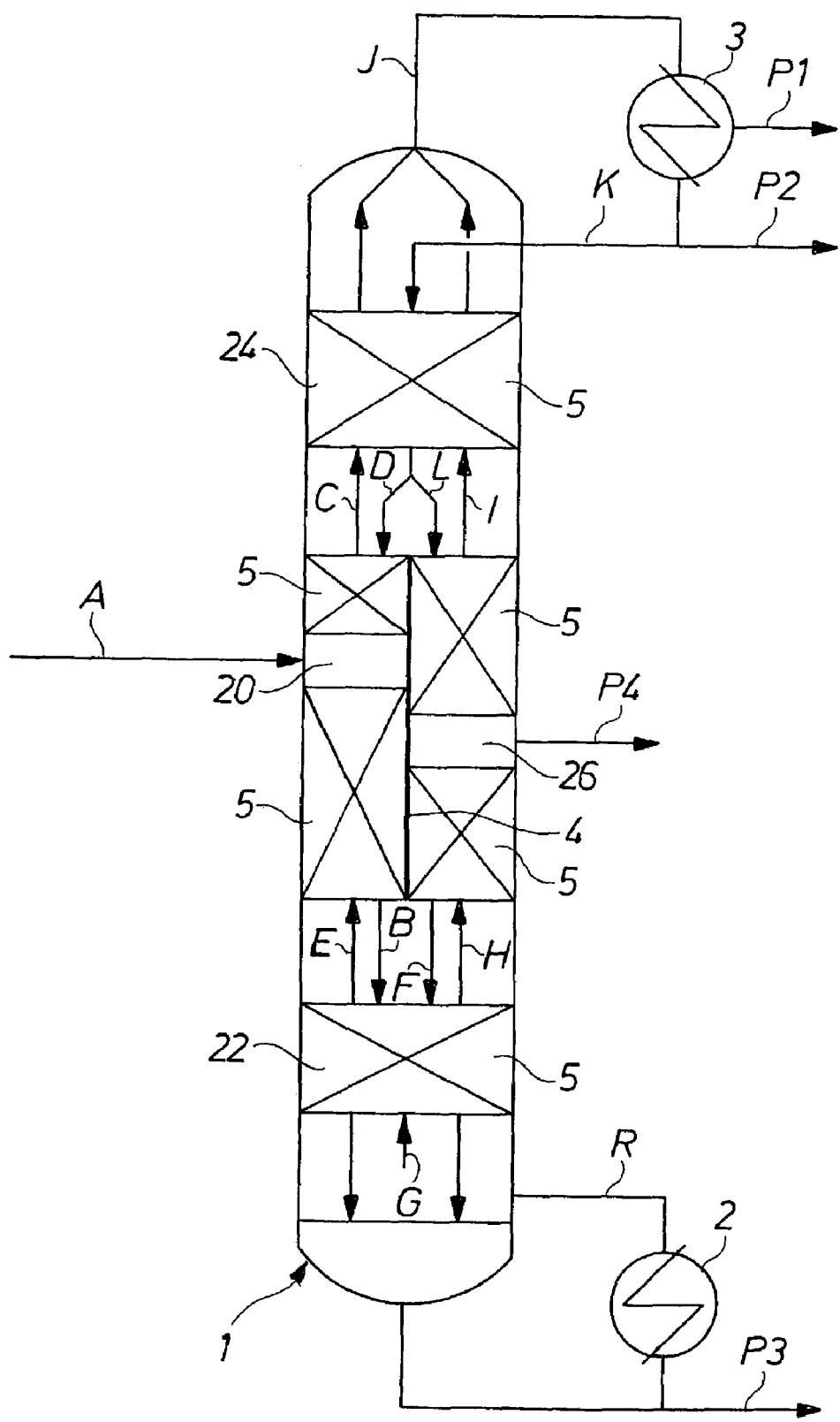
FIG. 1 is a schematic diagram of a dividing-wall distillation column.

As used herein, unless otherwise expressly specified, all of the numerical ranges, amounts, values and percentages such as those for amounts of materials, times and temperatures of reaction, ratios of amounts, values for molecular weight, and others in the following portion of the specification may be read as if prefaced by the word "about" even though the term "about" may not expressly appear with the value, amount or range.

The invention is directed to a process for the purification of toluenediisocyanate from a crude distillation feed comprising toluenediisocyanate, an organic solvent and less than 2% by weight phosgene by separating the crude distillation feed in a dividing-wall distillation column into at least four product fractions P1–P4, whereby P1 is a phosgene enriched low-boiler product,
P2 is a solvent-enriched product,
P3 is a high boiler enriched bottoms and
P4 is a toluenediisocyanate product stream.

The invention is also directed to a process for the production of toluenediisocyanate comprising the steps
a) reacting toluene diamine with phosgene resulting in a crude distillation feed,
b) separating the phosgene from the crude distillation feed from step a) if the crude distillation feed from step a) comprises 2% by weight or more of phosgene resulting in a crude distillation feed comprising less than 2% by weight phosgene,
c) separating the crude distillation feed comprising toluenediisocyanate, an organic solvent and less than 2% by weight phosgene in a dividing-wall distillation column into at least four product fractions P1–P4, whereby P1 is a phosgene enriched low-boiler product,
P2 is a solvent-enriched product,
P3 is a high boiler enriched bottoms and
P4 is a toluenediisocyanate product stream.

Preferebly the invention is directed to a process for the purification of toluenediisocyanate from a crude distillation feed comprising toluenediisocyanate, an organic solvent and less than 2% by weight phosgene by separating the crude distillation feed in a dividing-wall distillation column into four product fractions P1–P4, whereby P1 is a phosgene enriched low-boiler product,
P2 is a solvent-enriched product,
P3 is a high boiler enriched bottoms and
P4 is a toluenediisocyanate product stream.

Preferably the invention is also directed to a process for the production of toluenediisocyanate comprising the steps
a) reacting toluene diamine with phosgene resulting in a crude distillation feed,
b) separating the phosgene from the crude distillation feed from step a) if the crude distillation feed from step a) comprises 2% by weight or more of phosgene resulting in a crude distillation feed comprising less than 2% by weight phosgene,
c) separating the crude distillation feed comprising toluenediisocyanate, an organic solvent and less than 2% by weight phosgene in a dividing-wall distillation column into four product fractions P1–P4, whereby P1 is a phosgene enriched low-boiler product,
P2 is a solvent-enriched product,
P3 is a high boiler enriched bottoms and
P4 is a toluenediisocyanate product stream.

The phosgenation according to step a) is performed according to the state of the art. Toluene diamine is reacted with phosgene in the presence of a solvent solution in the liquid phase or with phosgene directly in the gas phase with a solvent used in the quench cooling of said reaction. The resulting reaction mixture preferably has a composition of 5–40% by weight toluenediisocyanate, 1–2% by weight hydrogen chloride, 1–5% by weight phosgene, 0.1–2% by weight high-boilers (polymeric isocyanates, hydrolyzable chloride compounds (HCC)), and the rest being solvent. Hydrolyzable chloride compounds are generally defined as compounds in which the available chlorine is "loosely" bound. Illustrative of these compounds are the following species: $ClCH_2C_6H_3(NCO)_2$ and $(CH_3NCOCl)CH_3C_6H_3(NCO)$.

Content of hydrolyzable chloride compounds are generally determined by reacting the available chlorine in the sample with a hot water-alcohol solution resulting in HCl and a subsequent titration to determine the hydrolyzable chlorine concentration. This value is generally reported as weight fraction hydrolyzable chlorine" (HC).

Chlorinated aromatic hydrocarbons are species in which the chlorine is "tightly" bound. Illustrative of such compounds are the common solvents o-dichlorobenzene, and chlorobenzene, and related compounds.

After the reaction the resulting reaction mixture is fed to a separation step b) if the reaction mixture (crude distillation feed) comprises 2% by weight or more of phosgene. In this separation step, the excess phosgene is at least partly removed resulting in crude distillation feed comprising less than 2% by weight of phosgene. The separation of the phosgene can be performed using many different methods or combinations thereof. Examples of these methods are simple vapor/liquid flash separation, with or without the increase of temperature or a decrease in pressure, gas stripping, distillation, etc.

The resulting crude distillation feed comprising less than 2% by weight of phosgene is then fed to a dividing-wall distillation column according to step c) and separated into four fractions (P1–P4).

Product Fraction P1 is a phosgene-enriched low-boiler product preferably comprising 20–50% by weight phosgene and other low boilers such as chlorobenzene, tetrachloromethane, trichloromethane and dichloromethane, 20–49% by weight solvent, the rest being noncondensable gases, i.e. air, hydrogen chloride, etc. The condensable species are preferably recovered and returned to the dephosgenation or excess phosgene recovery process.

Product Fraction P2 is a solvent enriched product which is then preferably reused in the phosgenation or excess phosgene recovery process. The fraction P2 preferably comprises solvent with an isocyanate concentration and a phosgene concentration of less than 100 ppm by weight, respectively.

Product Fraction P3 is a high-boiler enriched bottoms product which is preferably sent to a residue removal system for the further recovery of volatiles. The fraction P3 preferably comprises 0.5–15% by weight high-boilers (polymeric isocyanates, hydrolyzable chloride compounds (HCC), and other non-volatiles), the rest being toluenediisocyanate.

Product Fraction P4 is the isocyanate product stream. The fraction P4 preferably comprises less than 200 ppm by weight of solvent and/or chlorinated aromatic hydrocarbons (in total), less than 100 ppm by weight hydrolyzable chlorine (HC), less than 40 ppm by weight acidity, with a toluenediisocyanate concentration of at least 99.5% by weight.

In addition, an optional middle-boiler enriched product stream which is disposed or further processed for the recovery of solvent and/or TDI is obtained. Examples for middle boilers are trichlorobenzene and isocyanatotoluene.

As used herein, unless otherwise expressly specified, a low-boiler product or fraction refers to a product or fraction having a boiling temperature below the solvent. A high-boiler product or fraction refers to a product or fraction having a boiling temperature above the TDI.

The fractionation process including a dividing-wall distillation column may be successfully utilized to produce four main product streams from a partially to fully dephosgenated TDI reaction product resulting from the reaction of toluene diamine with phosgene in the presence of a solvent solution or from this reaction in the gas phase with a solvent used in the quench cooling after the reaction. The resulting distillation feed contains phosgene and other low-boiling components, solvent, toluene diisocyanates, hydrolyzable chloride compounds, and high-boiling residues. The four products are a phosgene-enriched low-boiler product P1, which is recovered and returned to the dephosgenation or excess phosgene recovery process, a relatively pure solvent product P2 which is then reused in the phosgenation or excess phosgene recovery process, a high-boiler enriched (polymeric isocyanate, hydrolyzable chloride compounds, and other non-volatiles) bottoms product P3 which is sent to a residue removal system for the further recovery of volatiles, and an isocyanate product stream P4. The solvent to be used can be any suitable solvent, preferably o-dichlorobenzene, p-dichlorobenzene, chlorobenzene, toluene, benzene, nitrobenzene, anisole, xylene, or any mixture thereof. Depending on reaction conditions different concentrations of TDI in the crude distillation feed can be obtained.

The process according to the present invention is performed in a dividing-wall distillation column such as that illustrated in FIG. 1. This dividing-wall distillation column is at least equipped with one reboiler and one condenser. The reboiler can be any of the standard types commonly found in the chemical industry, including in part falling-film evaporators, forced circulation evaporators, pool boiling (kettle) evaporators, natural circulation evaporators, etc. The condenser can be any of the types in common use in the chemical industry including co-current and countercurrent (knockback condensers). The column can be equipped with any mass transfer internals that are in common use in the chemical industry. These include, in part, sieve trays, valve trays, fixed valve trays, as well as structured or random distillation packings.

In one embodiment of the present invention (FIG. 1), the crude distillation feed is fed directly to a dividing-wall distillation column resulting in the four product fractions and product streams P1 to P4. In this embodiment the crude distillation feed has a preferred concentration of from 20–60% by weight, more preferred of from 25–50% by weight, and most preferred of from 30–40% by weight TDI.

In a second embodiment of the current invention, a separate additional preliminary fractionation column using standard distillation techniques is used to remove a portion of the solvent from the crude distillation feed before feeding to the dividing-wall distillation column. In this step, the partial removal of the solvent is preferably performed to produce an isocyanate-enriched product containing from 20 to 80% by weight TDI, with a preferred range from 25 to 60% TDI. The resulting products from this additional preliminary fractionation step are a phosgene-enriched low-boiler fraction, a solvent fraction, and an isocyanate and high-boiler enriched bottoms product.

Figure 2:
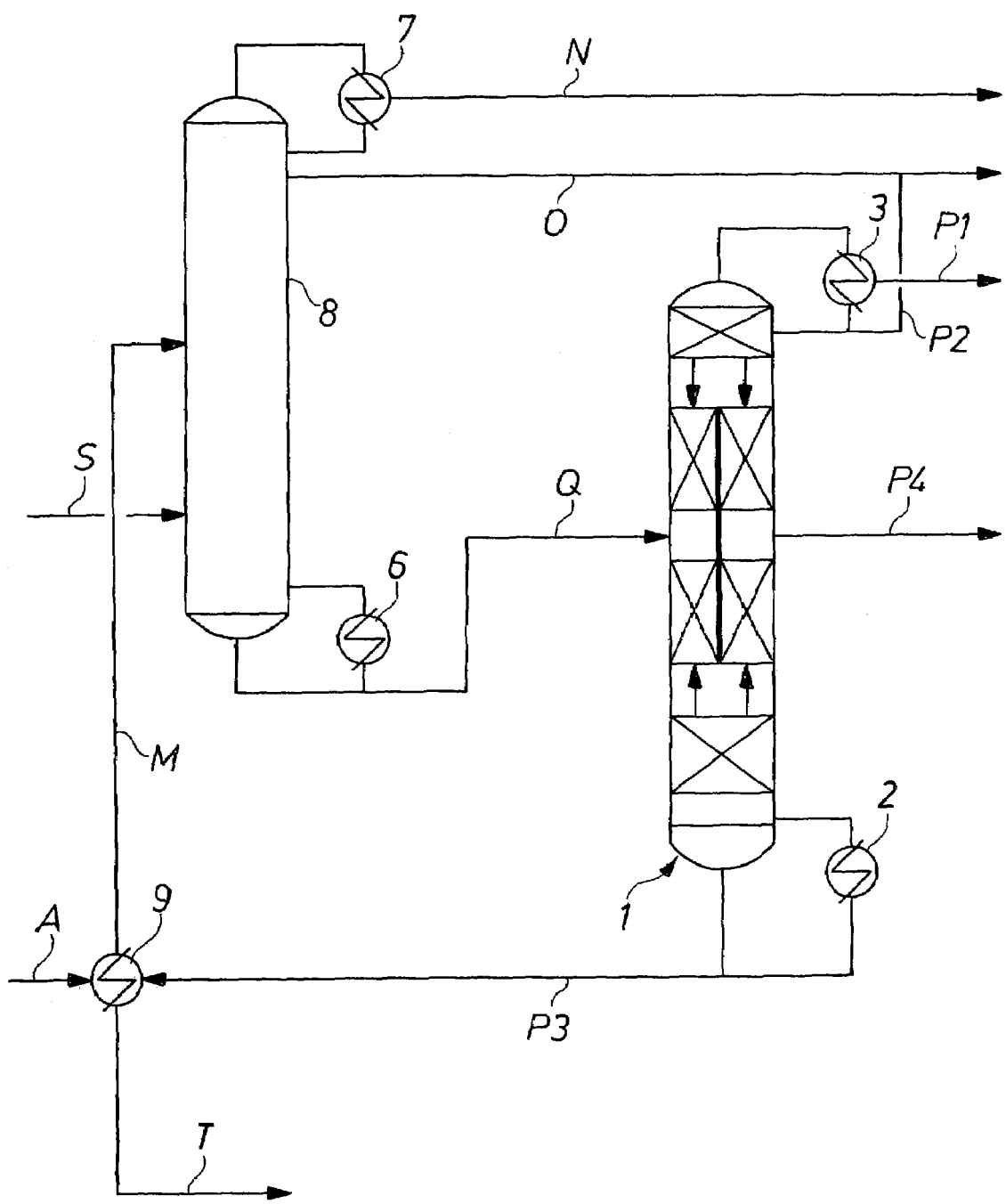
FIG. 2 is a flow schematic diagram of a dividing-wall distillation column used in combination with a device for performing pre-evaporation.

The additional preliminary fractionation can be performed with pre-evaporation in an apparatus such as that illustrated in FIG. 2. This preliminary fractionation step takes advantage of the solvent's lower boiling point than the isocyanate, allowing the majority of the solvent to be removed under higher pressure, therefore, reducing the necessary investment cost for the solvent removal. The crude distillation feed in this embodiment has a preferred isocyanate concentration of from 5–40% by weight, most preferably from 8–30% by weight. The pre-evaporation will preferably be performed at a temperature from 120–190° C. The additional preliminary fractionation is preferably operated in such a way that the bottoms product temperature is between 120–190° C.

Figure 3:
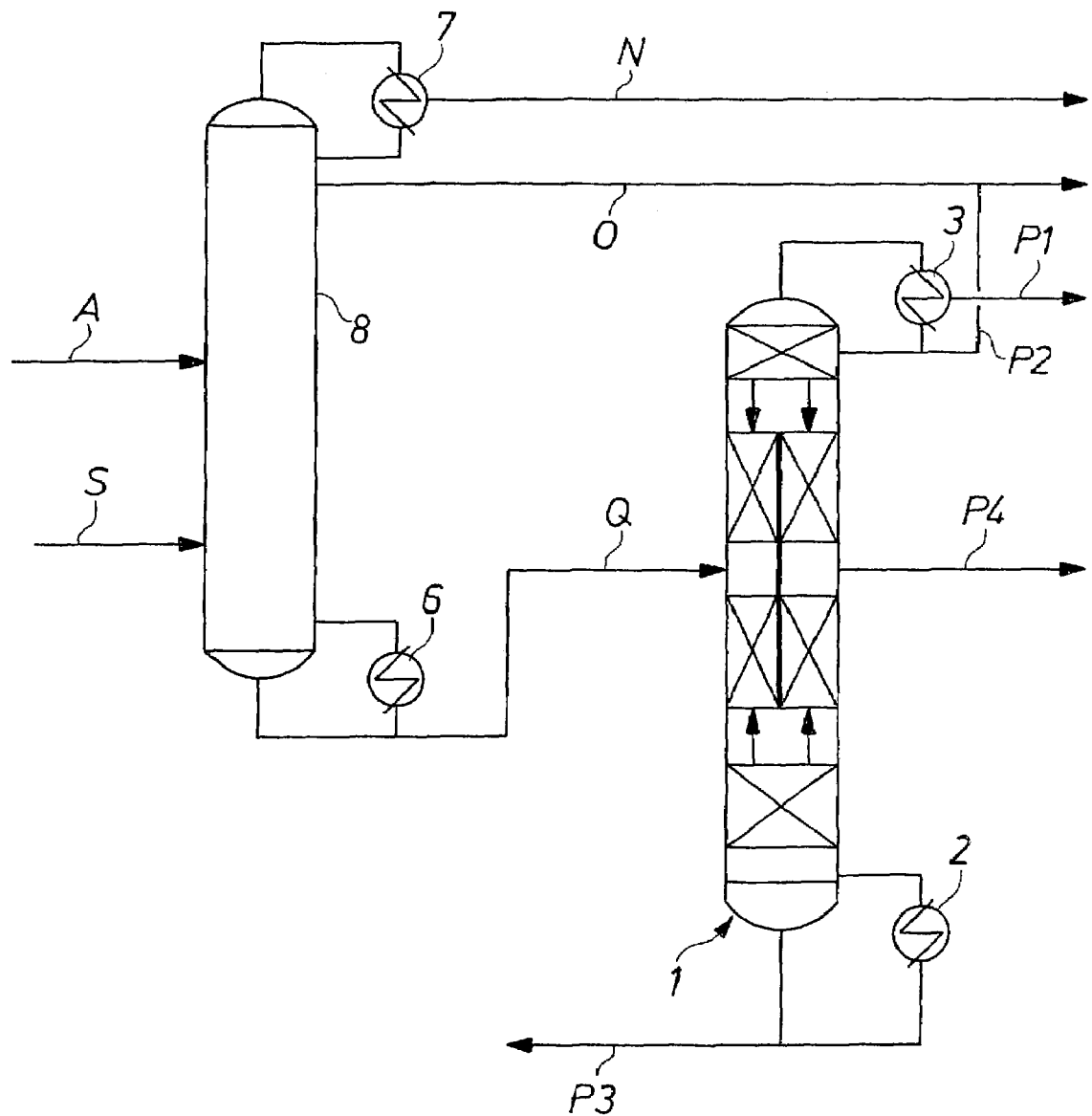
FIG. 3 is a flow schematic diagram of a device for performing preliminary fractionation without pre-evaporation.

The additional preliminary fractionation can also be performed without pre-evaporation in an apparatus such as that illustrated in FIG. 3. In this embodiment of the process the crude distillation feed is introduced as a liquid phase to the preliminary solvent removal step. The isocyanate concentration in the crude distillation feed is preferably from 5–40% by weight, more preferably from 8–30% by weight. The fractionation is preferably operated in such a way that the bottoms product temperature is between 120–190° C.

The invention is described in more detail in the following with reference to the accompanying drawings, wherein FIG. 1 shows a schematic of the dividing wall distillation column which is used in the process for the purification of mixtures of TDI, and FIG. 2 shows a flow schematic according to one preferred embodiment of the present invention wherein a portion of the solvent is removed in an additional preliminary fractionation column with pre-evaporation, and FIG. 3 shows a flow schematic according to one preferred embodiment of the present invention wherein a portion of the solvent is removed in an additional preliminary fractionation column without pre-evaporation.

FIG. 1 shows a dividing-wall distillation column 1 which is equipped with a reboiler 2, a condenser 3, a dividing-wall 4 and mass transfer internals 5.

The dividing wall distillation column 1 is divided into four distinct operating zones, a prefractionation zone 20 where the feed A is introduced, a stripping zone 22 with the high-boiler product P3, a main fractionation zone 26 with the isocyanate product P4, and a rectifying zone 24 with a vapor phase low-boiler product P1, and a liquid-phase solvent product P2. The prefractionation zone 20 and the main fractionation zone 26 lie side by side in the dividing wall distillation column 1 with a dividing-wall 4 separating the two zones.

Prefractionation Zone

The crude distillation feed A is fed to the prefractionation zone 20, wherein it is separated into two streams, a residue and a hydrolyzable chloride compound (HCC)-enriched liquid TDI stream B and a solvent and low-boiler enriched vapor stream C. This separation is effected by two streams, one liquid D and one vapor E. The liquid stream D, containing both solvent and TDI, enters the prefractionation zone from the rectifying zone. The vapor stream E, containing TDI and HCC's enters the prefractionation zone from the stripping zone.

Stripping Zone

The liquid product B from the prefractionation zone 20 as well as the TDI and HCC-containing liquid product F from the main fractionation zone enters the upper section of the stripping zone 22. Vapor G generated from the reboiler 2 in stream R causes the separation of intermediate component from the heavy component. The resulting residue-enriched liquid containing highboiler is routed away as the bottoms product stream P3. The column is designed for an operating pressure so that the temperature achieved in the reboiler will preferably be in the range of from 140–190° C. The TDI-enriched vapor streams E and H are fed to the prefractionation zone and the main fractionation zone respectively. The distribution of the vapor flow to the prefractionation zone and main fractionation zone is effected by the inherent pressure drop in the respective column section.

Rectifying Zone

The low-boiler enriched vapor products C from the prefractionation zone 20 and I from the main fractionation zone 26, both containing intermediate as well as low-boiling components enters the rectifying zone 24 at the lower section. The vapor product J from the rectifying zone 24 is fed to a condenser 3, and then a portion of the condensate product generated from the condenser is returned as reflux K to the top of the rectifying zone 24 causing the separation of light component from the intermediate component. The remaining fraction of the condenser liquid product is routed away as the solvent product stream P2. The uncondensed vapor product from the condenser is the low-boiler product stream P1. Internal reflux within the column generates a liquid stream. This liquid stream, containing mainly solvent and TDI, is divided into streams L and D which are routed to the main fractionation zone 26 and to the prefractionation zone 20, respectively. The proportional distribution of these liquid streams are controlled to achieve the required product quality.

Main Fractionation Zone

A TDI-enriched vapor product stream H from the stripping zone enters the main fractionation zone 26 from the bottom. A portion of the liquid product L from the rectifying zone 24 enters the main fractionation zone 26 from the top. The resulting fractionation generates three products: a vapor feed I to the rectifying zone 24, and a liquid feed F to the stripping zone 22, and a side draw product P4 that contains the desired quality isocyanate product.

FIG. 2 shows a flow schematic wherein a portion of the solvent is removed in an additional preliminary fractionation column 8 with pre-evaporation. The additional preliminary fractionation column 8 is equipped with a reboiler 6 and a condenser 7.

The crude distillation feed A and the high-boiler enriched liquid-phase P3 from the dividing-wall distillation column 1 are mixed and evaporated in a heat-exchanger 9, resulting in a vapor product M, which is fed to the preliminary fractionation column 8 and a residue-enriched liquid bottoms product T, which is fed to the residue removal process (not shown in FIG. 2). The vapor phase M as well as a liquid stream S containing the volatiles recovered in the residue removal system are then fractionated in the preliminary fractionation column 8 to achieve a phosgene and low-boilers enriched stream N, a nearly pure solvent product O containing less than 100 ppm by weight isocyanate, and an isocyanate-enriched bottoms product Q. The solvent fraction O is preferably re-used in the phosgenation or excess phosgene recovery step. The subsequent isocyanate-enriched bottom product Q is then introduced to the dividing-wall distillation column 1 resulting in the product streams P1–P4. In this embodiment, the high-boiler enriched product stream P3 from the dividing-wall distillation column 1 is returned to the pre-evaporation step (heat exchanger 9). In this embodiment, the preliminary solvent removal in the preliminary fractionation column 8 allows the reduction of the residence time of high-boiler containing mixtures in heated zones, allowing a better product yield.

FIG. 3 shows a flow schematic wherein a portion of the solvent is removed in an additional preliminary fractionation column 8 without pre-evaporation.

The crude distillation feed A is introduced as a liquid phase to the preliminary solvent removal step (additional preliminary fractionation column 8). The crude distillation feed A as well as a liquid stream S containing the volatiles recovered in the residue removal system are then fractionated to achieve a phosgene and low-boilers enriched stream N, a nearly pure solvent product O containing less than 100 ppm by weight isocyanate, and an isocyanate-enriched bottoms product Q containing almost all of the residues resulting from the reaction. The solvent fraction O is preferably re-used in the phosgenation or excess phosgene recovery step. The subsequent isocyanate-enriched bottom product Q is then introduced to the dividing-wall distillation column 1 resulting in the product streams P1–P4, with P3 fed to the residue removal system. The resulting process achieves a lower energy requirement at the expense of longer residence times of high-boiler containing mixtures in heated zones, thus leading to reduced product yield.

EXAMPLES

Example 1

Example 1 has been performed in a dividing-wall distillation column 1 of the type shown in FIG. 1.

A crude reaction mixture, containing 1000 kg/h toluenediisocyanate is completely dephosgenated and the dephosgenated reaction product is mixed with solvent from process sources (i.e. washers, vacuum systems, etc.), and the volatiles recovered from the residue removal to yield a crude distillation feed A at a temperature of 138° C., which is in the liquid phase at atmospheric pressure. The crude distillation feed A has the following composition by weight: 39.59% toluenediisocyanate (TDI), 0.61% TDI-residue, 0.06% hydrolyzable chloride compounds (HCC), 0.04% low-boilers and noncondensables, with the rest being o-dichlorobenzene. This crude distillation feed A is introduced to a packed dividing-wall distillation column 1 equipped with a single condenser 3 and falling-film reboiler 2, with structured distillation packing 5. The dividing-wall distillation column 1 has 7 theoretical stages in the rectification zone, 7 theoretical stages in the stripping zone, and a center fractionation zone with a dividing-wall 4 achieving a prefractionation zone and a main fractionation zone with 21 theoretical stages respectively. The crude distillation feed A partially vaporizes as it is introduced to the dividing-wall distillation column 1, because the dividing-wall distillation column 1 is operating at a pressure below the saturation pressure of the crude distillation feed stream A. The resulting liquid is mixed with a liquid stream taken from the rectification zone D and fed to the top of the packing 5 in the prefractionation zone, which then undergoes an initial prefractionation facilitated by the liquid feed to the top of the pre-fractionation zone and the vapor E entering the bed from the stripping zone. The resulting vapor from the flashing feed is mixed with the vapor product C from the prefractionation zone. This stream C is fed to the rectification zone.

The liquid product B from the pre-fractionation zone as well as the liquid product F from the main-fractionation zone are fed to the stripping zone. The dividing-wall distillation column 1 is operated with a pressure of approximately 118 mbar in the condenser 3 with a pressure drop across the system of 36 mbar. This allows for a temperature at a 10% vaporization, of 180° C. in the vapor G exiting the reboiler 2. The removal rate from the sump of the column is controlled to achieve a 10% weight residue concentration in the sump product P3. The resulting sump product P3 has a flow rate of 153 kg/h and has a composition by weight of 10% residue, 0.8% hydrolyzable chlorides compounds (HCC), the rest being TDI. The vapor G from the reboiler 2 enters the stripping zone. The resulting vapor products E and H are fed to the pre-fractionation zone and the main fractionation zone, respectively.

The vapor products C and I from the pre-fractionation zone and the main fractionation zone are fed to the rectification zone. The condenser 3 is operated at 118 mbar with a gas outlet temperature of stream P1 of 58° C. There are approximately 1.6 kg/h resulting uncondensed vapor and noncondensables (Stream P1) with a composition of 34% by weight solvent, the rest being non-condensable. The condensed liquid is partially returned to the column as reflux K to achieve the desired solvent quality. In this embodiment, a reflux ratio of 1.04 is maintained to achieve 1854 kg/h o-dichlorobenzene solvent with a TDI concentration of 10 ppm by weight (Stream P2). The reflux K produces an internal reflux in the column, resulting in a liquid product from the rectification zone which is normally divided into two fractions (D and L). In this case, however, there is no liquid fed from the rectification zone to the prefractionation zone (D=0 kg/h).

The liquid product L from the rectification zone is fed to the main fractionation zone where the final fractionation is performed using the vapor feed H from the stripping zone to achieve the isocyanate product P4 at the specified quality. The side draw is operated to achieve an internal reflux to side product ration of 1.09:1. This results in a product P4 of approximately 1000 kg/hr with no solvent, and a hydrolyzable chlorine (HC) concentration of less than 70 ppm and a product quality greater than 99.95%.

The specific energy usage for this case is 0.38 kW-h/kgTDI. This represents a 23% savings in energy in comparison to the state of the art described in the *Polymer Handbook*, and a 22.0% energy savings as compared to the state of the art described in *Industrielle Aromatencheme*. No comparison was made to the state of the art described in Chem Systems' *PERP Report for TDI/MDI*, because the low solvent concentration in the crude distillation feed A does not require a three column system.

Example 2

Example 2 has been performed in a distillation system including a preliminary solvent removal step (preliminary distillation column 8) with pre-evaporation in a heat exchanger 9 and a dividing-wall distillation column 1 such as that illustrated in FIG. 2.

A crude reaction mixture is completely dephosgenated and the dephosgenated reaction product mixed with solvent from process sources (i.e. washers, vacuum systems, etc.), to yield a crude distillation feed A containing 1250 kg/h toluenediisocyanate, at a temperature of approximately 152° C., which is in the liquid phase at atmospheric pressure. The crude distillation feed A has the following composition by weight: 9.74% toluenediisocyanate (TDI), 0.17% TDI-residue, 0.005% hydrolyzable chloride compounds (HCC), 0.01% low-boilers and noncondensables, with the rest being o-dichlorobenzene. This crude distillation feed A is fed together with the bottoms product P3 from the dividing-wall distillation column 1 to an evaporator (heat exchanger 9). P3 has a temperature of approximately 180 degrees and a saturation pressure of approximately 140 mbar. The mass flowrate of P3 is 167 kg/h and the composition by weight is 0.16% residue, 0.85% HCC, the rest being TDI. In the evaporator 9 a majority of the liquid feed is evaporated and fed as a vapor stream M to the preliminary fractionation column 8. The residue-enriched bottoms product T from the evaporator 9 is fed to the residue removal system. The operating temperature and pressure for the evaporator are 134° C. and 131 mbar. Stream M has a flowrate of 12778 kg/h and a weight composition of 0.01% low-boilers and inerts, 10.2% TDI, 2 ppm residue, 0.01% HCC, the rest being o-dichlorobenzene (ODB). Stream T has a flowrate of 222 kg/h and a composition of 10% residue, 0.11% hydrolyzable chloride compounds (HCC), 39.6% ODB, the rest being TDI.

The preliminary fractionation column 8 is equipped with a single condenser 7 and a single reboiler 6. It has 15 theoretical stages, with the vapor feed M to the bottom mass transfer stage. A liquid feed S which contains the recovered volatiles from the residue removal system is fed to the sump of the preliminary fractionation column S. Stream S has a temperature of 40° C. and a composition by weight of 0.09% hydrolyzable chloride compounds (HCC), 0.01% residue, 43.36% ODB, with the rest being TDI. The preliminary fractionation column 8 has a top pressure of 120 mbar and a pressure drop across the column system of 15 mbar. The condenser 7 is operated at a temperature of 67° C., resulting in an vapor phase product N of approximately 3 kg/h, with a composition by weight 54% non-condensables, 46% low-boiling condensables and solvent. Stream N is further processed and the recovered condensables are returned to phosgenation or phosgene recovery. The preliminary fractionation column 8 is designed to provide 2 theoretical stages between the condenser 7 and the solvent side-draw to produce a solvent stream O which is lean in low-boilers (i.e. phosgene)). The preliminary fractionation column 8 is operated with a reflux ratio of 0.3 to achieve a TDI concentration less than 10 ppm by weight in the solvent product O with the rest being ODB. Stream O has a flowrate of 10473 kg/h and is used in the phosgenation or in the phosgenation recovery process. The bottom product Q from the preliminary fractionation column 8 has a flowrate of 2502 kg/h and a composition by weight 43.36% ODB, 0.01% residue, and 0.08% hydrolyzable chloride compounds (HCC), with the rest being TDI.

Stream Q is fed to a dividing-wall distillation column 1 according to FIGS. 1 and 2 equipped with a single condenser 3 and falling-film reboiler 2, with structured distillation packing 5. The column has 7 theoretical stages in the rectification zone, 7 theoretical stages in the stripping zone, and a center fractionation zone with a dividing-wall 4 achieving a prefractionation zone and a main fractionation zone with 21 theoretical stages.

The dividing-wall distillation column 1 is operated with a pressure of approximately 105 mbar in the condenser 3 with a pressure drop across the system of 36 mbar. This allows for a temperature for 10% vaporization, of 180° C. in the vapor G exiting the reboiler 2. The removal rate from the sump of the dividing-wall distillation column 1 is controlled to achieve a bottoms product (P3) flowrate of 167 kg/h.

The condenser 3 is operated at 105 mbar with a gas outlet temperature of stream P1 of 83° C. There is approximately 1 kg/h resulting uncondensed vapor and noncondensables (Stream P1) with a composition of 76% by weight solvent, the rest being non-condensable. The condensed liquid is partially returned to the column as reflux K to achieve the desired solvent quality. In this embodiment, a reflux ratio of 1.94 is maintained to achieve 1084 kg/h o-dichlorobenzene solvent with a TDI concentration of 10 ppm by weight (Stream P2). The reflux K produces an internal reflux in the dividing-wall distillation column 1, resulting in a liquid product from the rectification zone which is normally divided into two fractions D and L. In this case the split ratio D:L relationship is 1:19. The liquid product L from the rectification zone is fed to the main fractionation zone where the final fractionation is performed using the vapor feed H from the stripping zone to achieve the isocyanate product P4 at the specified quality. The side draw is operated to achieve an internal reflux to side product ration of 0.56:1. This results in a product P4 of approximately 1250 kg/hr with no solvent, and a hydrolyzable chlorine (HC) concentration of less than 70 ppm and a product quality greater than 99.95%.

The specific energy usage for this case is 1.047 kW-h/kgTDI. This represents a 7% savings in energy in comparison to the state of the art described in the *Polymer Handbook*, a 9% energy savings as compared to the state of the art described in *Indutrielle Aromatenchemie*, and a 7% savings over the state of the art described in Chem Systems' *PERP Report for TDI/MDI*

Example 3

Example 3 was performed in a distillation system including a preliminary solvent removal step (preliminary fractionation column 8) without pre-evaporation and a dividing-wall distillation column 1 such as that illustrated in FIG. 3.

A crude reaction mixture was completely dephosgenated and the dephosgenated reaction product was mixed with solvent from process sources (i.e. washers, vacuum systems, etc.) to yield a crude distillation feed A containing 1250 kg/h toluenediisocyanate, at a temperature of approximately 148° C., which is in the liquid phase at atmospheric pressure. The crude distillation feed had the following composition by weight: 23.4% toluenediisocyanate (TDI), 0.41% TDI-residue, 0.015% hydrolyzable chloride compounds (HCC), 0.03% low-boilers and noncondensables, with the rest being chlorobenzene. This crude distillation feed A was fed along with the volatile species S from the residue removal process to the preliminary fractionation column 8.

The preliminary fractionation column 8 has 11 theoretical stages, with the liquid feeds A and S to the second from bottom mass transfer stage. Stream S has a temperature of 38° C. and a composition by weight of 0.63% hydrolyzable chloride compounds (HCC), 0.12% residue, with the rest being TDI. The preliminary fractionation column 8 has a top pressure of 130 mbar and a pressure drop across the column system of 12 mbar. The condenser 7 is operated at a temperature of 50.7° C., resulting in an vapor phase product N of approximately 7 kg/h, with a composition by weight 22% non-condensables and 78% low-boiling condensables and solvent. Stream N is further processed with the recovered condensables returned to phosgenation of phosgene recovery. The preliminary fractionation column 8 is designed to provide 2 theoretical stages between the condenser 7 and the solvent side-draw to allow for the production of a solvent product (stream O) which is lean in low-boilers (i.e. phosgene)). The preliminary fractionation column 8 is operated with a reflux ratio, of 0.04. The solvent product stream O has a flowrate of 3072 kg/h and a weight composition of 10 ppm TDI, the rest being chlorobenzene. Stream O is used in the phosgenation or in the phosgenation recovery process. The bottom product Q from the preliminary fractionation column 8 has a flowrate of 2455 kg/h and a composition by weight of 40% chlorobenzene, 0.01% residue, 0.08% hydrolyzable chloride compounds (HCC), with the rest being TDI.

Stream-Q is fed to a dividing-wall distillation column 1 according to FIGS. 1 and 3 equipped with a single condenser 3 and falling-film reboiler 2, with structured distillation packing 5. The dividing-wall distillation column 1 has 3 theoretical stages in the rectification zone, 7 theoretical stages in the stripping zone, and a center fractionation zone with a dividing-wall 4 achieving a prefractionation zone and a main fractionation zone with 8 theoretical stages.

The dividing-wall distillation column 1 is operated with a pressure of approximately 107 mbar in the condenser 3 with a pressure drop across the system of 19 mbar. This allows for a temperature for 10% vaporization, of 180° C. in the vapor G exiting the reboiler 2. The removal rate from the sump of the dividing-wall distillation column 1 is controlled to achieve a bottoms product (P3) flowrate of 222 kg/h.

The condenser 3 is operated at 105 mbar with a gas outlet temperature of stream P1 of 46° C. There is approximately 1 kg/h resulting uncondensed vapor and noncondensables (Stream P1) with a composition of 76% by weight solvent, the rest being non-condensable. The condensed liquid is partially returned to the column as reflux K to achieve the desired solvent quality. In this embodiment, a reflux ratio of 2.19 is maintained to achieve 981 kg/h chlorobenzene solvent with a TDI concentration of 10 ppm by weight (Stream P2). The reflux K produces an internal reflux in the column, resulting in a liquid product from the rectification zone which is normally divided into two fraction D and L. In this case the split ratio D:L relationship is 1:19. The liquid product L from the rectification zone is fed to the main fractionation zone where the final fractionation is performed using the vapor feed H from the stripping zone to achieve the isocyanate product P4 at the specified quality. The side draw is operated to achieve an internal reflux to side-draw product ration of 0.70:1. This results in a product P4 of approximately 1250 kg/hr with no solvent, and a HC concentration of less than 70 ppm and a product quality greater than 99.95%.

The specific energy usage for this case is 0.42 kW-h/kgTDI. This represents a 19% savings in energy in comparison to the state of the art described in the *Polymer Handbook*, an 26% energy savings as compared to the state of the art described in *Indutrielle Aromatenchemie*, and a 30% savings over the state of the art described in Chem Systems' *PERP Report for TDI/MDI*.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of toluenediisocyanate comprising the steps of:
    a) reacting toluene diamine with phosgene resulting in a crude distillation feed,
    b) separating the phosgene from the crude distillation feed from step a) when the crude distillation feed from step a) comprises 2% by weight or more of phosgene, resulting in a crude distillation feed comprising less than 2% by weight phosgene,
    c) separating the crude distillation feed comprising toluene-diisocyanate, an organic solvent and less than 2% by weight phosgene in a dividing-wall distillation column into at least four product fractions P1–P4, whereby
    P1 is a phosgene enriched low-boiler product,
    P2 is a solvent-enriched product,
    P3 is a high boiler enriched bottoms and
    P4 is a toluenediisocyanate product stream.

2. The process of claim 1 wherein the phosgene enriched low-boiler product P1 comprises 20–50% by weight phosgene and other low boilers, 20–49% by weight solvent, and noncondensible gases.

3. The process of claim 1 wherein the solvent-enriched product fraction P2 comprises solvent with a isocyanate concentration of less than 100 ppm by weight and a phosgene concentration less than 100 ppm by weight.

4. The process of claim 1, wherein the high boiler enriched bottoms fraction P3 comprises toluenediisocyanate and 0.5–15% by weight high-boilers.

5. The process of claim 1, wherein the toluenediisocyanate product stream fraction P4 has a toluenediisocyanate concentration of at least 99.5% by weight and comprises less than 200 ppm by weight of solvent and/or chlorinated aromatic hydrocarbons, less than 100 ppm by weight hydrolyzable chlorine (HC) and less than 40 ppm by weight acid.

6. The process of claim 1, wherein the solvent is at least one of o-dichloro-benzene, p-dichlorobenzene, chlorobenzene, toluene, benzene, nitrobenzene, anisole, or xylene.

7. The process of claim 1, wherein after the removal of phosgene in step b) the solvent is partially removed from the crude distillation feed before feeding the crude distillation feed to the dividing-wall distillation column according to step c).

8. The process of claim 7, wherein the solvent is partially removed to produce an isocyanate-enriched product containing from 20 to 80% by weight toluenediisocyanate.

9. The process of claim 7, wherein the crude distillation feed from step b) is pre-evaporated before the solvent is partially removed.

* * * * *